United States Patent [19]

Barbone

[11] Patent Number: 5,007,833
[45] Date of Patent: Apr. 16, 1991

[54] BUTTRESS CHANNEL

[75] Inventor: Norman K. Barbone, Mansfield, Ohio

[73] Assignee: Implant Plastics Corporation, Mansfield, Ohio

[21] Appl. No.: 550,661

[22] Filed: Jul. 10, 1990

[51] Int. Cl.$^5$ .................. A61C 13/12; A61C 13/225; A61C 8/00
[52] U.S. Cl. ................................. 433/172; 433/173; 433/174
[58] Field of Search ............... 433/172, 173, 174, 176, 433/167, 190, 181, 182

[56] References Cited

U.S. PATENT DOCUMENTS 3,748,739  7/1973  Thilbert ............................. 433/173
4,556,388  12/1985  Hader ................................. 433/181

*Primary Examiner*—John J. Wilson
*Assistant Examiner*—C. Cherichetti
*Attorney, Agent, or Firm*—Fay, Sharpe, Beall, Fagan, Minnich & McKee

[57] ABSTRACT

A structural element for forming a transition joint between a support bar and an associated mounting sleeve in the fabrication of support structure for holding prosthetic teeth. The element is precision molded of plastic and comprises a solid elongated body with an outwardly open elongated recess extending longitudinally of the body. The recess is sized to closely engage the associated mounting sleeve throughout the length of the recess. On the side of the body opposite the recess, there is an outwardly open elongated groove having a width to resiliently engage the support bar. In its preferred form, the groove and the recess have longitudinal axes which are in the same plane to assure that the support bar is in alignment with the axis of the support sleeve. Also, the recess has a generally semi-cylindrical configuration sized to conform to the exterior of the support sleeve and to make contact therewith throughout its length.

12 Claims, 2 Drawing Sheets

FIG. 3
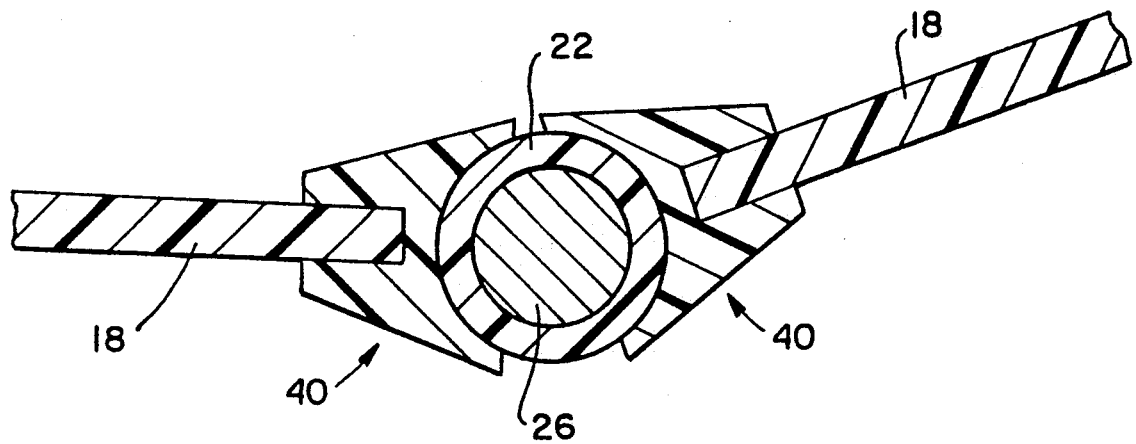
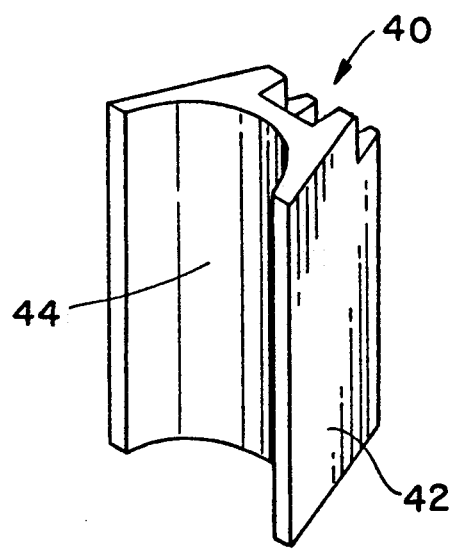
FIG. 4

BUTTRESS CHANNEL

BACKGROUND OF THE INVENTION

The subject invention is directed toward the art of dental devices and appliances and, more particularly, to articles for facilitating the manufacture or formation of dental implant attachment structures.

During the formation of support structure for mounting or insertion in dental implant anchoring means for the purpose of holding prosthetic teeth, it is generally required to form a precise pattern of the necessary support structure. The pattern is then used for direct or indirect molding of the support structure in high strength material.

The process of forming the patterns is generally quite difficult and time consuming and involves fabricating support bar assemblies that join between the screws or pins which extend outwardly of the gum tissue from the anchors or attachment elements implanted in the alveolar bone. Typically, the pattern for the support bar assembly is formed by positioning sleeves on each of the screws and then connecting the support bar patterns between adjacent sleeves and joining the ends of the bars to the associated sleeves with wax or a suitable adhesive. As can be appreciated, the bars must each be individually cut to a precise length and then joined to the sleeves. It is very difficult and time consuming to produce good transition joints between the bar ends and the associated sleeves.

BRIEF STATEMENT OF THE INVENTION

The subject invention overcomes the above difficulties and provides an arrangement which greatly facilitates the fabrication of the support bar assemblies.

In accordance with one aspect, the subject invention provides a structural element for forming a transition joint between a support bar and an associated mounting sleeve in the fabrication of support structure for holding prosthetic teeth. The element is precision molded of plastic and comprises a solid elongated body with an outwardly open elongated recess extending longitudinally of the body. The recess is sized to closely engage the associated mounting sleeve throughout the length of the recess. On the side of the body opposite the recess, there is an outwardly open elongated groove having a width to resiliently engage the support bar. In its preferred form, the groove and the recess have longitudinal axes which are in the same plane to assure that the support bar is in alignment with the axis of the support sleeve.

In accordance with another aspect of the invention, the recess has a generally semi-cylindrical configuration sized to conform to the exterior of the support sleeve and to make contact therewith throughout its length.

Preferably, and in accordance with a more limited aspect, the body tapers in thickness from the recess side to the groove side. This produces a connecting joint with a smooth transition from the sleeve to the bar.

With the use of the structural element described, the bar pattern is effectively located and temporarily held in place relative to the mounting sleeves during waxing or adhesive bonding. With the recess of generally semi-cylindrical form, the bar is held in position at any desired angular location relative to the sleeve. That is, the bars join the sleeves through what is effectively a hinge joint until the bonding is complete. As can be appreciated, this greatly facilitates the forming of the pattern for the support bar assembly.

SUMMARY OF THE INVENTION

Accordingly, a primary object of the invention is the provision of structural components which facilitate the forming of dental implant attachment structures.

A still further object of the invention is the provision of an attachment element for providing a smooth transition joint between support bars and support screw structures in structures used for mounting to, or connecting with, dental implant anchoring structures.

A further object is the provision of a precision molded component which allows support bars to be readily joined to support cylinders in the formation of dental implant attaching assemblies.

A still further object is the provision of a device of the type described which is relatively simple to use and which will hold the various components in place until the actual final bonding is completed.

BRIEF DESCRIPTION OF THE DRAWINGS

The above and other objects and advantages will become apparent from the following description when read in conjunction with the accompanying drawings wherein:

FIG. 3 is a cross-sectional view taken generally on line 3—3 of FIG. 1; and,

FIG. 4 is a pictorial view of one of the structural elements used in the assembly of FIG. 1.

DETAILED DESCRIPTION OF THE PREFERRED EMBODIMENT

Figure 1:
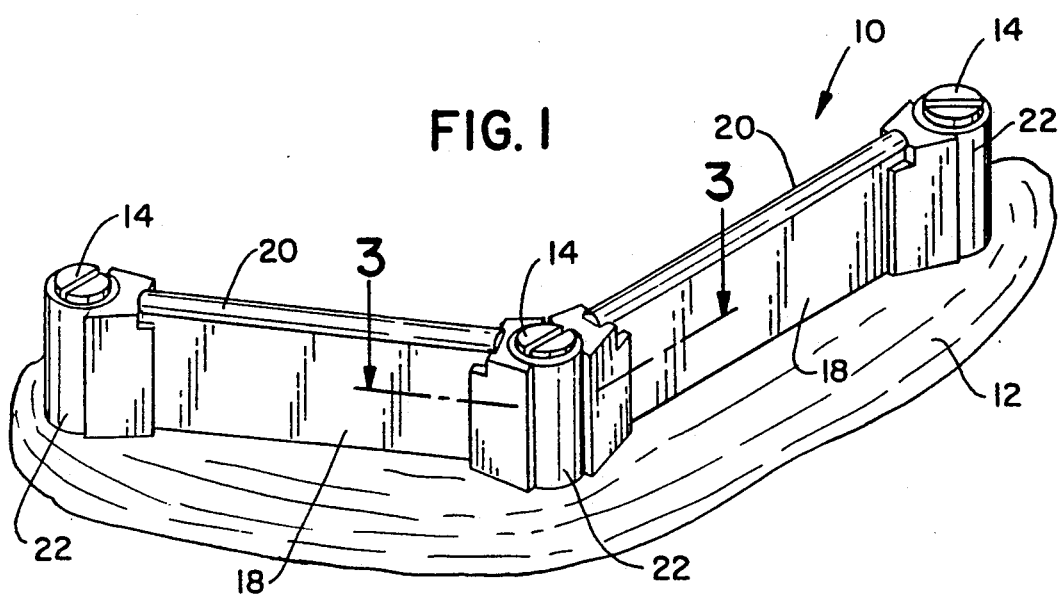
FIG. 1 is a pictorial view showing a bar type assembly in position on suitable screws which extend into anchors implanted in the alveolar bone.

Referring more particularly to the drawings wherein the showings are for the purpose of illustrating a preferred embodiment of the invention only, and not for the purpose of limiting same, FIG. 1 shows the overall arrangement of a pattern structure to be used for forming through either direct or indirect molding a support structure for holding prosthetic teeth in place on dental implant anchors positioned in the alveolar bone. The support structure pattern assembly 10 is illustrated as being assembled and connected in place on the patient's gum 12 by suitable mounting screws 14 which are threaded, as shown at 16 in FIG. 2, and extend into the threaded open upper ends of the bone mounted anchoring means (not illustrated). The pattern assembly 10 is comprised of suitable bar members 18 which extend generally between the mounting screws 14 and have a central web generally of uniform thickness with a bead or enlarged upper rim 20 which provides a connecting bead for being resiliently received in a suitable snap connector formed internally of the prosthetic teeth structure (not shown). The terminal ends of the bar members 18 are suitably connected or provided with means to allow them to be connected to the mounting screws 14.

As discussed, the components of the subject assembly, as illustrated in the drawings, are the components which form the pattern from which the final support assembly is formed in a suitable high strength material. The components used in forming the pattern are preferably precision molded from a plastic having the requisite properties to serve either as a direct or indirect pattern.

Figure 2:
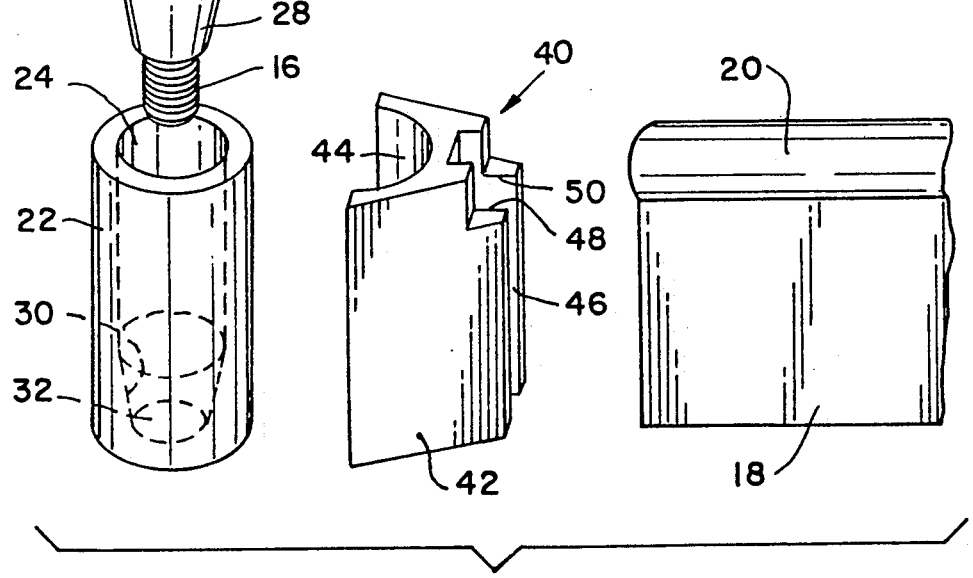
FIG. 2 is an exploded pictorial view of the major components used to make up the assembly of FIG. 1.

In accordance with the subject invention, the various structural components which function to connect the bar members is with the associated mounting screws 14 comprise a first sleeve member 22 which is arranged to be received on the mounting screws 14 and fixed in place through connection of the screws into the implanted connectors or anchoring means (not shown). Specifically, as shown in FIG. 2, the first sleeve member 22 includes a central opening 24 which is sized so as to closely receive the barrel 26 of the mounting screw 14. The mounting screw 14 is provided with a tapered conical section 28 that leads to the reduced diameter threaded portion 16. The interior of the central opening 24 in the first sleeve member 22 is provided with a complimentary shaped tapered lower end 30 which connects with a lower opening 32. Lower opening 32 is, of course, sized so as to allow passage of the threaded portion 16 freely therethrough. As can be appreciated from the arrangement described, the mounting screws 14 thus serve to suitably mount the individual first sleeve members 22 to the associated jaw mounted anchoring points and to hold the first sleeve members 22 in place during installation of the bar members 18.

According to the invention, the structural elements 40 used to connect the bar member 18 to the associated first sleeve members 22 comprise, in the preferred embodiment, a buttress-like channel member which can be best seen in FIGS. 2 and 4. The structural element 40 is precision molded from a suitable plastic and comprises a generally elongated body 42 which is solid and relatively rigid. One side of the elongated body 42 is provided with an inwardly extending recess 44 which is sized to closely engage the exterior of the first sleeve members 22 as illustrated in FIGS. 1 and 3. Preferably, the recess 44 has a generally semi-cylindrical shape with its surface located on a radius substantially equal to the radius of the first sleeve member 22. Although the arcuate extent of recess 44 could vary, it is preferably greater than about 60 degrees.

As mentioned, the recess 44 extends axially of the elongated body 42 so that the elongated body 42 and the associated first sleeve member 22 have their longitudinal axes in the same plane when they are assembled as shown in FIGS. 1 and 3.

The structural element 40 further includes a longitudinally extending groove 46 which is located along the side of the elongated body 42 directly opposite the recess 44. The groove 46 is in alignment with the axis of the elongated body 42 and extends inwardly thereof to a uniform depth throughout its length as shown. The side walls 48 and 50 of the groove 46 are spaced apart a distance which is preferably slightly less than the thickness of the main central web portion of the bar member 18. Preferably, the spacing is such that when the bar member 18 is inserted into the groove 46, as illustrated in FIGS. 1 and 3, the groove 46 resiliently engages and temporarily holds the bar member 18 in the desired assembled relationship. The structural element 40 thus assures that the bar member 18 lies in a plane which is in general alignment with the axis of the mounting screw 14 and the associated anchoring member (not shown).

Because of the manner in which the ends of the bar member 18 are engaged and held by the groove 46, the forming of the bar member and its sizing is somewhat simplified. Note that slight deviations in the required length of the bar members 18 during the manufacturing or the forming of the pattern assembly 10 are compensated for by the ability of the bar member 18 to be moved in and out of the associated groove 46. When the assembly is formed as shown in FIG. 1, the various components can be bonded together through the use of suitable solvents, cements, waxing, or the like. Thereafter, the thus bonded and joined assembly can be cast in a more rigid material for remounting in the mouth of the patient.

In addition to facilitating the formation of the support structure patterns, it should be noted that the buttress-like structural element 40 has a thickness which tapers from the wider recess 44 to the narrower groove 46. This provides a relatively smooth contoured connection between the individual first sleeve members 22 and the thinner bar members 18.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

Having described the invention, it is now claimed:

1. A structural element for forming a transition joint between a support bar and an associated mounting sleeve in the fabrication of support structure for holding prosthetic teeth, said structural element comprising:
a solid elongated body molded of a resinous plastic material, an outwardly open recess extending longitudinally of the body along a first side thereof, said recess being sized and adapted throughout its length to closely engage an exterior of said mounting sleeve in a direction axially thereof, an outwardly open elongated groove having a width to resiliently engage the support bar, said groove extending longitudinally of the body along a second side opposite said first side, said second side being narrower than said first side and said body tapering in thickness from said first side to said second side.

2. The structural element as defined in claim 1 wherein said groove and said recess each have respective longitudinal axes which are coplanar.

3. The structural element as defined in claim 1 wherein said groove has longitudinally extending parallel sides.

4. The structural element as defined in claim 1 wherein said recess is of general cylindrical shape and has an arcuate extent of greater than 60 degrees.

5. The structural element as defined in claim 1 wherein said groove and said recess have respective longitudinal axes which are parallel.

6. The structural element as defined in claim 1 wherein said groove is of uniform depth throughout its length.

7. A structural element for forming a transition joint between a support bar and an associated mounting sleeve in the fabrication of support structure for holding prosthetic teeth, said structural element comprising:
an elongated body formed of a resinous plastic material with an outwardly open recess extending longitudinally of the body along a first side thereof, said recess being contoured and sized to closely engage an exterior of said mounting sleeve in a direction axially thereof, an outwardly open elongated groove having a width to receive the support bar, said groove extending longitudinally of the body along a second side opposite said first side.

8. The structural element as defined in claim 7 wherein said groove and said recess each have respective longitudinal axes which are coplanar and wherein said body tapers in thickness from said first side to said second side.

9. The structural element as defined in claim 8 wherein said groove has longitudinally extending parallel sides.

10. The structural element as defined in claim 9 wherein said recess is of general cylindrical shape and has an arcuate extent of greater than 60 degrees.

11. The structural element as defined in claim 7 wherein said groove and said recess have respective longitudinal axes which are parallel.

12. The structural element as defined in claim 11 wherein said groove is of uniform depth throughout its length.

* * * * *